United States Patent [19]

O'Donnell, Jr.

[11] Patent Number: 5,651,377

[45] Date of Patent: Jul. 29, 1997

[54] LASER ADJUSTABLE SUTURE

[76] Inventor: Francis E. O'Donnell, Jr., 709 The Hamptons La., Town & Country, Mo. 63017

[21] Appl. No.: 600,248

[22] Filed: Feb. 12, 1996

Related U.S. Application Data

[63] Continuation-in-part of Ser. No. 445,900, May 22, 1995.
[51] Int. Cl.⁶ .................................................... A61B 19/00
[52] U.S. Cl. ............................................ 128/898; 606/228
[58] Field of Search ............................ 128/898; 606/4, 606/5, 232, 228, 215–216

[56] References Cited

U.S. PATENT DOCUMENTS

| | | | |
|---|---|---|---|
| 5,090,425 | 2/1992 | Stahl | 128/898 |
| 5,234,006 | 8/1993 | Eaton et al. | 128/898 |
| 5,464,424 | 11/1995 | O'Donnell, Jr. | 606/232 X |

*Primary Examiner*—Lee S. Cohen
*Assistant Examiner*—Ryan Carter
*Attorney, Agent, or Firm*—Paul M. Denk

[57] ABSTRACT

A laser adjustable surgical suture and method of using the same. The adjustable suture comprises components that contract when exposed to laser energy and components that relax when exposed to laser energy. By selectively applying predetermined laser energy to the appropriate component, the suture can be contracted to increase tension or relaxed to relieve tension. In another embodiment, a surgical laser is used to ablate suture material from the suture so as to selectively weaken the suture and allow it to stretch and relieve tension.

5 Claims, 2 Drawing Sheets

LASER ADJUSTABLE SUTURE

This application is a continuation-in-part of application Ser. No. 08/445,900, filed May 22, 1995, pending.

BACKGROUND OF THE INVENTION

This invention relates generally to ophthalmic surgery and, more specifically, to an adjustable suture and a method of wound closure that prevents unwanted induction of astigmatism.

Anterior segment ophthalmic surgical wound closure often has been associated with unwanted induction of astigmatism. In cataract implant surgery and in penetrating keratoplasty, the placement of radially orientated sutures is associated with a steepening of the curvature of the cornea in the meridian, corresponding to the suture, as shown in FIG. 1 and as will be described below. This steepening of the curvature results in an astigmatic refractive error with the positive cylinder axis orientated along the steep meridian. In order to secure the wound and to avoid leakage of aqueous humor, the surgeon generally ties the suture very tight. If the suture is tied too loose, there can be a flattening of the cornea and leakage of aqueous humor. Furthermore, there can be a flattening of the cornea absent leakage due to shifting of the wound approximations. This flattening of the cornea, with or without leakage, also can lead to astigmatic refractive error with the positive cylinder axis orientated 90° to the meridian of the wound.

Efforts have been made to avoid unwanted astigmatic changes. For example, surgical techniques have been developed that create as small a wound, i.e. short arc of incision) as possible. This type of short arc incision is used in cataract implant surgery. In penetrating keratoplasty, the use of a continuous or running suture with post-operative adjustment of suture tension has been suggested to reduce astigmatism. None of these procedures has proved to be totally satisfactory in preventing post-surgical astigmatism.

As suggested above, post-operative adjustment of suture tension may reduce astigmatism. Therefore, it may be possible to adjust the focal point of the eye by the appropriate adjustment of a suture. Generally, nylon or cat-gut sutures are used to close the surgical wound. For the most part, surgical sutures can be loosened or tightened by untying the knot, drawing the suture tighter, and then retying the knot. In some situations, the suture must be snipped and retied or the suture must be removed and replaced. In delicate surgeries, for example ophthalmological surgery, it is quite difficult to adjust the tension on a suture once it is in place. The sutures placed in the eye are particularly fine. Adjusting the tension on the suture by conventional methods is painstaking and time consuming and can result in discomfort and inconvenience for the patient.

SUMMARY OF THE INVENTION

It is, therefore, among the principal objects of the present invention to provide a method of suturing an ophthalmic surgical wound which reduces distortion of the focal point of the eye and the incidence of unwanted astigmatism.

Another object of the invention is to provide a method for adjusting the focal point of the eye by the adjustment of the tension on a suture.

It is another object of the present invention to provide a suture that can be adjusted in a non-conventional manner.

Another object of the invention is to provide such a method that prevents leakage of aqueous humor.

Still another object of the present invention is to provide such a method that prevents flattening of the cornea.

A further object of the invention is to provide such a method that prevents disorientation of the positive cylinder axis.

It is an other object of the present invention to provide a surgical suture that reacts to laser energy by becoming longer or shorter so that the tension on the suture can be adjusted by apply a predetermined laser energy.

Yet another object of the invention is to provide a method of relaxing the tension on a surgical suture using photoablation.

A further object of the invention is to provide such a method that is safe and simple to practice, easy to learn and well suited to its intended purpose.

In accordance with the invention, briefly stated, a method of suturing an ophthalmic surgical wound is provided that prevents induction of unwanted astigmatism. The method employs a horizontal wound closure within the depth of the wound. The tension on the wound to cause approximation of the tissue does not result in corneal steepening. A radial or horizontal compression suture is provided that contracts under the application of laser energy to effect tightening of the suture or can be partially severed with the application of laser energy to effect a loosening of the suture. One embodiment of the suture is formed of concentric fibers with an outer clad of a non-elastic material and an inner core of laser reactive elastic material. Application of appropriate laser energy to the clad causes the suture to elongate and loosen. Application of appropriate laser energy to the elastic core causes the elastic inner core to contract and draw the suture tighter. In another embodiment, the suture has alternating segments of elastic and non-elastic material. The elastic material contracts under the application of laser energy and the non-elastic material elongates under the application of laser energy. In another method of loosening the suture a predetermined wavelength of laser energy is applied to a suture to photoablate and partially or completely sever the suture to effect loosening of the suture.

DESCRIPTION OF THE PREFERRED EMBODIMENT

Figure 1:
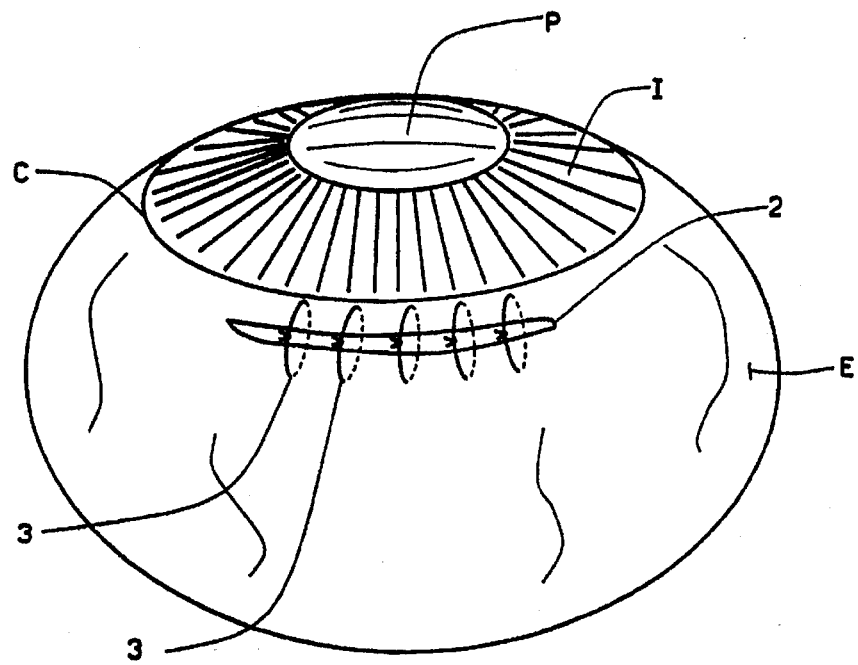
FIG. 1 is a perspective view of a human eyeball illustrating a conventional prior art suturing method.

FIG. 1 illustrates the prior art method of suturing a surgical wound in eyeball E. Eyeball E has the normal anatomic landmarks including the cornea C, iris I and pupil P. There is a surgical incision 2 proximate the iris I. The incision is made for cataract implant surgery or penetrating keratoplasty or the like. It will be appreciated that the suturing method of the present invention can be used to close any surgical incision without departing from the scope of the invention.

The surgical method of FIG. 1 employs a plurality of sutures 3. The exact number of sutures 3 depends upon the length of the incision. Sutures 3 extend across the incision and conform to the curvature of the eyeball, and arranged in a circular pattern across the wound incision. That is, the plane of suture tissue is vertical to the surface of the eyeball E. To prevent leakage, the suture takes a deep "bite" of tissue and must be drawn tight. If the suture 3 is too loose, a flattening of the cornea C, leading to astigmatic refractive error can occur with the positive cylinder axis orientated 90° to the meridian of incision 2.

Figure 2:
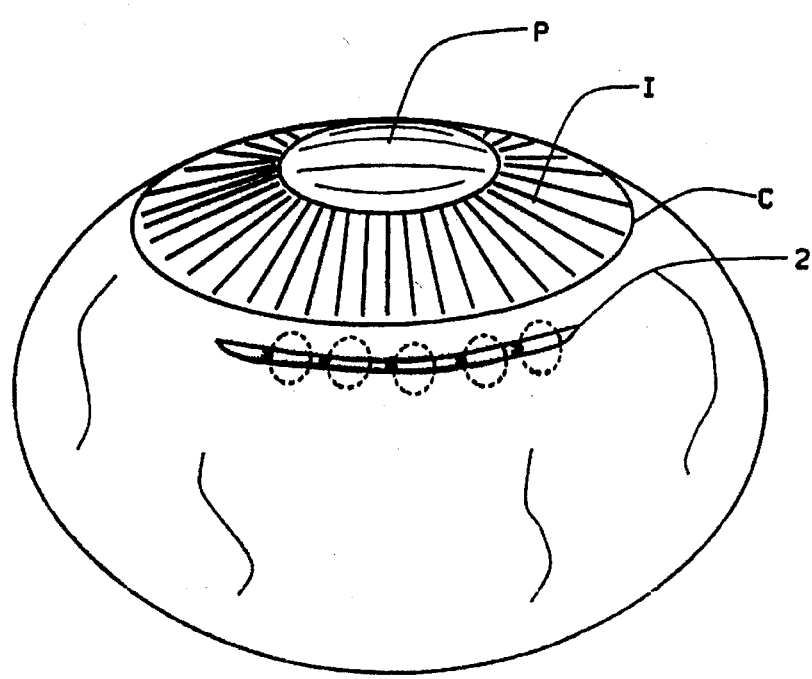
FIG. 2 is a perspective view of a human eyeball illustrating the suturing method of the present invention.

FIG. 2 illustrates the suturing method of the present invention. Sutures 3 are placed through the margin of the wound and extended horizontally along the incision 2 so that each suture 3 is substantially flat relative to the surface of the eyeball E. Thus the plane of sutured tissue is horizontal relative to the surface of eyeball E. The depth at which the suture is placed in the tissue is substantially reduced over the prior art method. For example, the bite of tissue is about one-fifth to one tenth that of the prior art. Therefore, less tissue is compressed. Furthermore, since the bite of tissue is parallel to the incision, it causes less compression across the wound, reducing the tendency to produce astigmatism. The effect on the focal point of the eye can be manipulated by the appropriate adjustment of the tension on the sutures. As stated above, conventional methods of adjusting the tension generally are not satisfactory. However, the present invention allows fine adjustment of the tension of the suture by the application of laser energy, as will now be described in detail.

Figure 3:
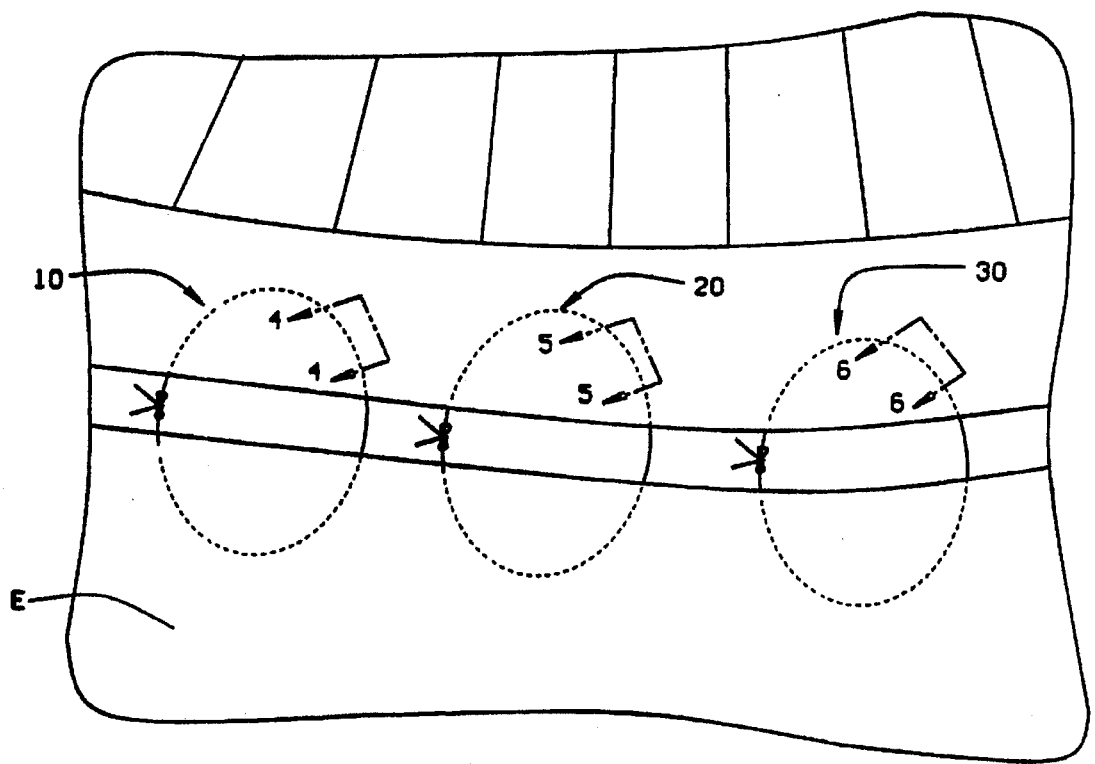
FIG. 3 is an enlarged partial section of a human eyeball with a sutured wound illustrating the placement of three different sutures.

FIG. 3 is an enlarged area of a sutured wound showing two embodiments of a laser adjusted suture of the present invention. One embodiment, indicated generally by reference numeral 10 is shown in greater detail in FIG. 4. Suture 10 is constructed from concentric fiber material. Suture 10 has an outer cladding 12 and a concentric inner fiber core 14. Outer cladding 12 is made of a transparent, relatively non-elastic material such as polyester. Inner fiber core 14 is constructed from relatively elastic, laser reactive deformable material such as nylon, mersaline, prolene or polymethylmethacrylate. It will be appreciated that core 14 is more elastic than cladding 12. Core 14 is darkly pigmented, for example blue, black or purple so as to readily absorb laser energy. To tighten suture 10, laser energy L1 is focused on core 14. Core 14 is heated to a temperature below vaporization, causing core 14 to contract and tighten the suture. To effect more tightening, a sequence of laser spots is placed along the length of core 14. To loosen suture 10, laser energy L1 is increased until core 14 breaks, relaxing some tension on suture 10. To effect more loosening, a plurality of breaks may be made along the length of core 14. Furthermore, laser energy may be directed to cladding 12 causing it to soften after core 14 is severed.

Figure 5:
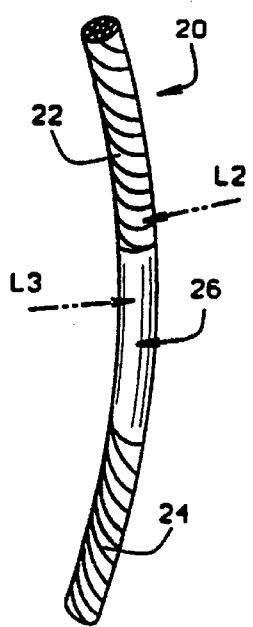
FIG. 5 is a cross-sectional view of a suture taken along lines 5—5 of FIG. 4.

FIG. 3 also illustrates a suture employing another embodiment of the laser adjustable suture of the present invention indicated generally by reference numeral 20, which is shown in greater detail in FIG. 5. Suture 20 is comprised of alternating links or segments. Segments 22 and 24, for example, are comprised of a laser reactive, relatively elastic deformable material such as nylon, mersaline, prolene or polymethylmethacrylate. Segment 26 is comprised of a less elastic material such as polyester. It will be appreciated that suture 20 can be constructed as long as necessary and comprised of a plurality of alternating segments of material such as 24 and 26. In use, laser energy L2 is applied to elastic segments, such as 24. Laser energy should be below the threshold for vaporization, for example, Argon laser at 200 mW for 0.2 seconds or shorter pulse duration. Application of laser energy L2 causes a contraction of the elastic material, thus tightening suture 20. To effect increased tightening of the suture, laser energy L2 can be applied to more than one elastic segment. Application of laser energy L3 to a non-elastic segment, such as 26, causes a weakening and lengthening of segment 26 and thus a lengthening of suture 20. This lengthening of the non-elastic segments results in less tension and loosening of the suture 20.

Figure 6:
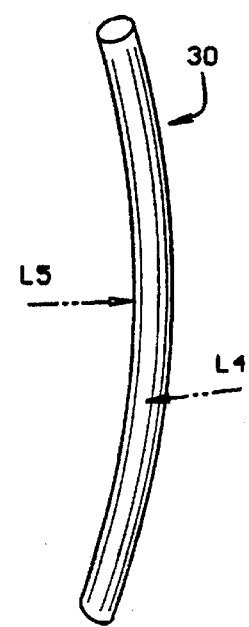
FIG. 6 is a cross-sectional view of a suture taken along lines 6—6 of FIG. 4.

FIG. 3 also illustrates the use of a monofilament suture, indicated generally by reference numeral 30, shown in greater detail in FIG. 6, having a dark, energy absorbing color or pigment, preferably black, for example a 10-0 monofilament nylon suture pigmented black. Treatment of the length suture 30 with appropriate laser energy will effect relaxation or lengthening of suture 30. On the other hand, treatment with an alterative laser energy will cause tightening or shortening of suture 30. For example, treatment of suture 30 with laser energy L4 at a wavelength of 532 nanometers (green wavelength), a spot size of 250 microns in diameter, an intensity of 200 milliwatts and a pulse duration of 0.1 seconds will achieve contraction of the suture 30. Studies have indicated application of energy L4 to the length of the suture material will result in a 30% to 40% shortening of the suture. For the opposite effect of suture relaxation or lysis, laser energy L5 comprised of a spot size of 50 microns in diameter and increased energy of 400 milliwatts per pulse at 0.1 seconds duration cause a relaxation of the suture up to a point where the suture could rupture, effecting complete release of tension.

Figure 4:
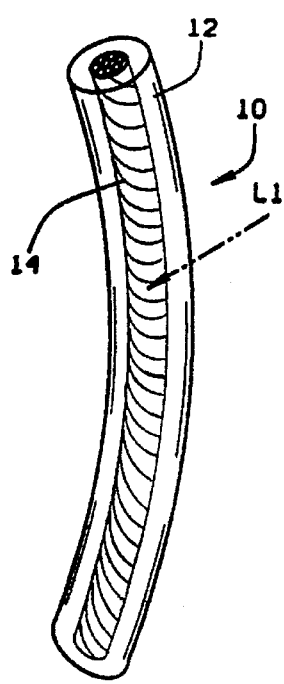
FIG. 4 is a cross-sectional view of a suture taken along lines 4—4 of FIG. 3.
Figure 7:
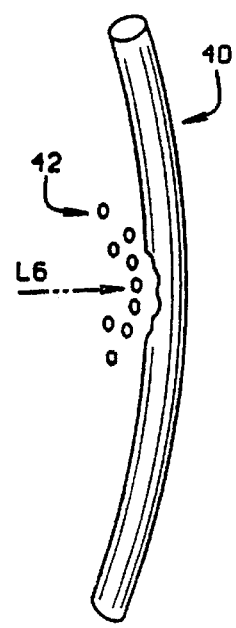
FIG. 7 is an enlarged section of a suture illustrating partial photoablation of the suture.

FIG. 7 illustrates an alternative method of the present invention. As will be appreciated, the method of the FIG. 7 employs the application of laser energy L6 to photo-ablate a suture 40 to weaken the tension on the suture. Generally speaking, the portion of the suture to be ablated lies on the surface of the eye in order to reduce the need to ablate overlying ocular tissue. Suture 40 may be any acceptable suture, for example a suture as illustrated in FIGS. 4–6, above, or any other conventional suture as long as it is not metallic. Laser energy L6 is applied to remove a small amount of the suture material 42 and thereby allow the tension on suture 40 to relax without totally severing or disrupting the suture. In the preferred embodiment, a Mini-Excimer Laser (LaserSight) is used because of its ability to deliver a small diameter pulse with low energy, 80 millijoules/cm$^2$, and deliver an extremely small spot size and to control the pattern of laser delivery.

It will be appreciated from the foregoing that the surgeon can adjust the focal point of the eye and/or prevent astigmatism by the appropriate adjustment of tension of the sutures. The surgeon can apply appropriate laser energy, as described above, and increase the tension thereby effectively flattening the cornea and shifting the focal axis. Further, the surgeon can apply appropriate laser energy to the appropriate suture to relax the tension and allow the cornea to assume a more rounded profile and thereby adjusting the focal axis.

It will be appreciated that various changes and modifications may be made in the method of the present invention without departing from the scope of the appended claims. Therefore, the foregoing description and drawings are intended to be illustrative only and should not be construed in a limiting sense.

I claim:

1. A method of suturing a wound through an ophthalmologic surgery incision in an eyeball comprising the steps of:

suturing the wound horizontally relative to a surface of the eyeball thereby causing less compression across the incision, said suturing accomplished by introducing a needle into a tissue margin of the wound, said needle having a suture material associated therewith;

moving the needle through the tissue horizontally relative to the surface of the eyeball to draw the wound together;

knotting the suture material;

withdrawing the needle;

adjusting the tension of the suture by applying a predetermined laser energy to the suture, to change a length of the suture, said introduction of the needle into the tissue at the margin of the wound being formed in a circular pattern, a portion of said circular pattern being located and embedded within the eye, while the remainder of the circular pattern is exposed within the wound of the eye and oriented arcuately within the surgical wound.

2. A laser adjustable suture comprising an elongated section of suture having an outer cladding and an inner core, said outer cladding comprised of a substantially non-elastic material and said inner core comprised of a relatively elastic material, said inner core being comprised of a substantially elastic material selected from the group consisting of nylon, mersaline, prolene, and polymethylmethacralate, the inner core of said suture being darkly pigmented, and said inner core contracts under the application of a predetermined laser energy, said laser energy being applied to the suture with a wave length of approximately 530 nanometers, a spot size of approximately 250 microns in diameter, and intensity of approximately 200 milliwatts, and a pulse duration of approximately 0.1 seconds.

3. A laser adjustable suture comprising, an elongated section of suture, said suture comprised of alternating segments of substantially elastic material and substantially non-elastic material, said substantially elastic material disposed to contract under an application of a predetermined amount of laser energy thereby decreasing an overall length of the section of suture, said non-elastic material formed of the suture as polyester, and the elastic material selected from the group consisting of nylon, mersaline, prolene, and polymethylmethacralate.

4. A method of adjusting the tension on a surgical suture comprising the steps of, focusing a laser on a section of suture material, said suture material being reactive when exposed to laser energy, activating said laser so as to emit laser energy, adjusting said suture material with said laser energy until a tension on said suture reaches a predetermined tension, the adjustment further comprises contacting the suture by exposing the suture to laser energy having a wave length of approximately 530 nanometers, a spot size of approximately 250 microns in diameter, an intensity of approximately 200 to 400 milliwatts, and a pulse duration of approximately 0.1 seconds.

5. A method of adjusting the tension on a surgical suture comprising the steps of, focusing a surgical laser on the suture, activating the surgical laser to emit laser energy, ablating a small spot on a surface of the suture with laser energy, removing fragments of surgical material from the suture surface thereby weakening the suture in the area of ablation to allow the suture to relax and relieve the tension on the suture, wherein the laser energy applied at approximately 80 millijoules or less.

* * * * *